United States Patent
Ma et al.

(10) Patent No.: US 9,830,514 B2
(45) Date of Patent: Nov. 28, 2017

(54) METHOD AND APPARATUS FOR DISTINGUISHING BETWEEN TYPES OF VEGETATION USING NEAR INFRARED COLOR PHOTOS

(71) Applicant: WEYERHAEUSER NR COMPANY, Federal Way, WA (US)

(72) Inventors: Zhenkui Ma, Kent, WA (US); Yuzhen Li, Shoreline, WA (US)

(73) Assignee: Weyerhaeuser NR Company, Seattle, WA (US)

( * ) Notice: Subject to any disclaimer, the term of this patent is extended or adjusted under 35 U.S.C. 154(b) by 29 days.

(21) Appl. No.: 14/142,341

(22) Filed: Dec. 27, 2013

(65) Prior Publication Data

US 2015/0186727 A1    Jul. 2, 2015

(51) Int. Cl.
    *G06K 9/46*     (2006.01)
    *G06K 9/00*     (2006.01)
    *G01N 21/17*     (2006.01)

(52) U.S. Cl.
CPC ......... *G06K 9/00657* (2013.01); *G01N 21/17* (2013.01); *G01N 2021/1797* (2013.01)

(58) Field of Classification Search
CPC ............... G06K 9/00657; G01N 21/17; G01N 21/1765; G01N 21/1797; G01N 2021/1797
See application file for complete search history.

(56) References Cited

U.S. PATENT DOCUMENTS

| | | | |
|---|---|---|---|
| 6,160,902 A * | 12/2000 | Dickson | G01J 3/2803 348/144 |
| 6,356,646 B1 | 3/2002 | Spencer | |
| 7,058,197 B1 * | 6/2006 | McGuire | G06K 9/00657 382/100 |
| 2004/0052730 A1 | 3/2004 | Hochman | |
| 2009/0022359 A1 | 1/2009 | Kang et al. | |
| 2010/0158314 A1 * | 6/2010 | Ma | G06K 9/00657 382/103 |
| 2010/0316292 A1 | 12/2010 | O'Hara et al. | |
| 2012/0155714 A1 | 6/2012 | Douglass et al. | |

OTHER PUBLICATIONS

Jasinski, "Estimation of Subpixel Vegetation Density of Natural Regions Using Satellite Multispectral Imagery", May 1996, IEEE, Transactions on Geoscience and Remote Sensing, vol. 34, No. 3, p. 804-813.*

(Continued)

*Primary Examiner* — Chan Park
*Assistant Examiner* — Timothy Choi
(74) *Attorney, Agent, or Firm* — Perkins Coie LLP

(57) ABSTRACT

A system for analyzing remotely sensed photos of a forest or other areas of interest uses a computer system to increase the variation in NIR data having values that represent items of interest. In one embodiment, a computer system applies a stretching function to the NIR data to increase their variation. The objective spectral stretched NIR data is used to differentiate different types of vegetation in the remotely sensed image. Objective-based Vegetation Index (OVI) values are calculated from the objective spectral stretched NIR data that allow different types of vegetation to be distinguished. In one embodiment, the OVI values are used to differentiate hardwoods from conifers in a digital aerial photo of a forest.

6 Claims, 6 Drawing Sheets

(56) References Cited

OTHER PUBLICATIONS

Wolter et al., "Improved Forest Classification in the Northern Lake States Using Multi-Temporal Landsat Imagery", Sep. 1995, American Society for Photogrammetry and Remote Sensing, Photogrammetric Engineering & Remote Sensing, vol. 61, No. 9, p. 1129-1143.*

Wikipedia, "Normalization (image processing)", Oct. 12, 2012, Wikipedia.org, <https://en.wikipedia.org/w/index.php?title=Normalization_(image_processing)&oldid=517345976>, p. 1-2.*

Liew, "Interpreting Optical Remote Sensing Images", Aug. 1, 2010, CRISP, Principles of Remote Sensing, <https://web.archive.org/web/20100801002051/http://www.crisp.nus.edu.sg/~research/tutorial/opt_int.htm>.*

Kim, "Contrast Enhancement Using Brightness Preserving Bi-Histogram Equalization", Feb. 1997, IEEE Transactions on Consumer Electronics, vol. 43, No. 1, p. 1-8.*

Driver, et al., "Preliminary Classification of Infrared Aerial Photographs using an Advanced Algorithm" GLSdevelopment.net, AARS, Asian Conference on Remote Sensing, (ACRS), ACRS 1999, Poster Session 1 (1999) p. 1, 4-7.

Alley, "Algorithm Theoretical Basis Document for Decorrelation Stretch" Jet Propulsion Laboratory, Version 2.2 Aug. 15, 1996 (Aug. 15, 1996), entire document, especially p. 5, 6 [online] URL=<http://www.dstretch.com/DecorrelationStretch.pdf.

Maas, Stephan, et al., "Use of Satellite Imagery to Radiometrically Calibrate Digital Airborne Multispectral Imagery," 20th Biennial Workshop on Aerial Photography, Videography, and High Resolution Digital Imagery for Resource Assessment 2005, Oct. 4-6, 2005, 9 pages.

Reutebuch, Steve, "LIDAR: An Emerging Tool for Multiple Resource Measurement, Planning and Monitoring", Western Forester, Society of American Foresters, Mar./Apr. 2008, pp. 1-5, vol. 53, US.

Haugerud, Ralph, "A Model Specification for LIDAR Surveys in the Pacific Northwest", Western Forester, Society of American Foresters, Mar./Apr. 2008, pp. 6-7, vol. 53, US.

McFadden, George, "Developing a Stand-Level Inventory Using LIDAR", Western Forester, Society of American Foresters, Mar./Apr. 2008, pp. 8-9, vol. 53, US.

Schiess, Peter, "The Impact of LIDAR Technology on Transportation System Design: Moving from Coarse Topographic Maps to Detailed Digital Elevation Models," Western Forester, Society of American Foresters, Mar./Apr. 2008, pp. 10-13, vol. 53, US.

* cited by examiner

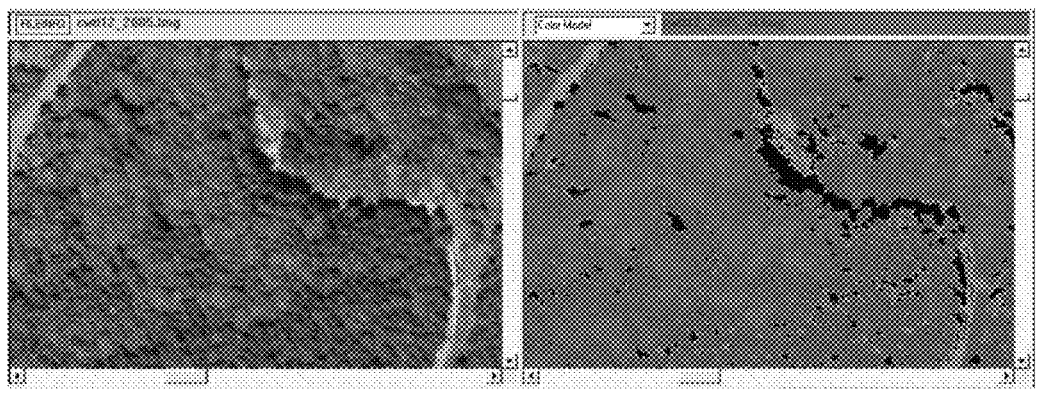
*FIG. 3A*                  *FIG. 3B*

METHOD AND APPARATUS FOR DISTINGUISHING BETWEEN TYPES OF VEGETATION USING NEAR INFRARED COLOR PHOTOS

TECHNICAL FIELD

The technology disclosed herein relates to systems and methods for analyzing digital aerial photos, and in particular to systems for analyzing images of forest lands in order to differentiate between different types of vegetation such as hardwoods and conifers.

BACKGROUND

In managed forests, there is an ongoing need to be able to inventory the types of trees that are growing in a given area. For example, in conifer forests, hardwood trees may be initially be viewed as an undesirable species that should be removed because they compete for water and nutrients with a desired species. However, if the hardwoods grow to such a size that they become harvestable, then the trees have their own value and should be inventoried.

As managed forests become increasingly large, it is becoming too costly to physically inventory all the areas of the forest. Therefore, remote sensing technology is becoming increasingly used to provide information about the types and ages of the trees that are in the forest. With remote sensing, aerial or satellite images of an area of interest in the forest are received that contain data for different spectral bands. From the remotely sensed images, the spectral data can be interpreted to provide information about the vegetation that is growing in the area of interest.

One commonly used measure of the spectral data is the Vegetation Index (VI). VI is most often calculated by dividing the near infrared spectral data received from a region of interest by the red light spectral data for the same region of interest. The Vegetation Index correlates with biomass growing in the area of interest. However, the conventional method of calculating VI is not very effective at differentiating between different types of vegetation in the area of interest.

SUMMARY

As will be explained in detail below, the technology disclosed herein relates to a system and method for analyzing aerial images in a manner that can differentiate between different types of vegetation and in particular, can differentiate hardwoods from conifers in the image. In one particular embodiment, near infrared (NIR) data from a digital aerial photo is mathematically manipulated or stretched to increase its variation. The stretched NIR data is used to compute Vegetation Index (VI) values that can be used to differentiate different types of vegetation in a remotely sensed image.

BRIEF DESCRIPTION OF THE DRAWINGS

FIG. 3A is a NIR Color photo created from objective spectral stretched NIR data in which hardwoods can be distinguished from conifers in accordance with one embodiment of the disclosed technology;

FIG. 3B is image created from objective-based VI (OVI) data calculated from objective spectral stretched NIR data in accordance with one embodiment of the disclosed technology;

DETAILED DESCRIPTION

As will be explained in detail below, the technology disclosed herein relates to a system for processing digital aerial photo data in order to be able to distinguish different types of vegetation in an area of interest. In one embodiment, near infrared (NIR) spectral data in a digital aerial photo is manipulated to increase its variation. A formula is selected that increases a distribution of the NIR spectral data values that are above a threshold and represent vegetation or other items of interest. With the formula, an input NIR data value from an image is re-mapped to the larger range of output NIR values.

The re-mapped or "Objective Spectral Stretched (OSS)" NIR data values can be viewed as a NIR color photo to determine if different types of vegetation for a region of interest in an image are visible. If so, the formula is applied to the NIR spectral data and the results are divided by the red light spectral values for the same region of interest in order to calculate Objective-based Vegetation Index (OVI) values. The OVI values can be processed to differentiate different types of vegetation.

In one embodiment, the OVI values can be displayed as color pixels in an image (e.g. assign RGB colors to each OVI value using their group average of NIR, Red, and Green bands), where the color of the pixel in the image indicates a type of vegetation. In another embodiment, a computer system can analyze the color of the pixels in an image to distinguish/inventory the types of vegetation in the area of interest.

Figure 1:
FIG. 1A is a NIR color photo created from digital aerial photo data in which is it difficult to separate hardwoods from conifers.
FIG. 1B is a NIR color photo created from objective spectral stretched NIR data in which hardwoods can be distinguished from conifers in accordance with one embodiment of the disclosed technology.

FIG. 1 illustrates a NIR color image that is created from spectral data in a digital photo of an area of interest. The digital photo is preferably an aerial image that captures data in at least a near infrared spectral band from 0.8 to 2.5 microns and a red spectral band data from 0.6 to 0.75 microns although the aerial image may also include spectral data for other spectral bands (e.g. green, far infrared etc.).

In the NIR color image shown in FIG. 1A, the red channel for the image is supplied with NIR data from the remotely sensed photo, the green channel for the image is supplied with the data values from the red spectral band from the same photo and the blue channel for the image is supplied with data from a green spectral band from the same photo. In the NIR color image, all the vegetation growing in the area of interest appears red in color and without enough variation in the color shades to be able to distinguish between different types of vegetation.

FIG. 1B shows a NIR color image that has been created from objective spectral stretched NIR data in accordance with the disclosed technology. The objective spectral stretched NIR data is supplied to the red channel and the green and blue channels are provided with the same data used creating the NIR color image shown in FIG. 1A. In the NIR color image shown in FIG. 1B, pixels representing conifer trees have a more pronounced green/blue component to their color and pixels representing hardwoods appear more red in color. With the NIR color image shown in FIG. 1B, a forester or computer can easily identify which trees are hardwoods and which trees are conifers in the image.

Figure 2:
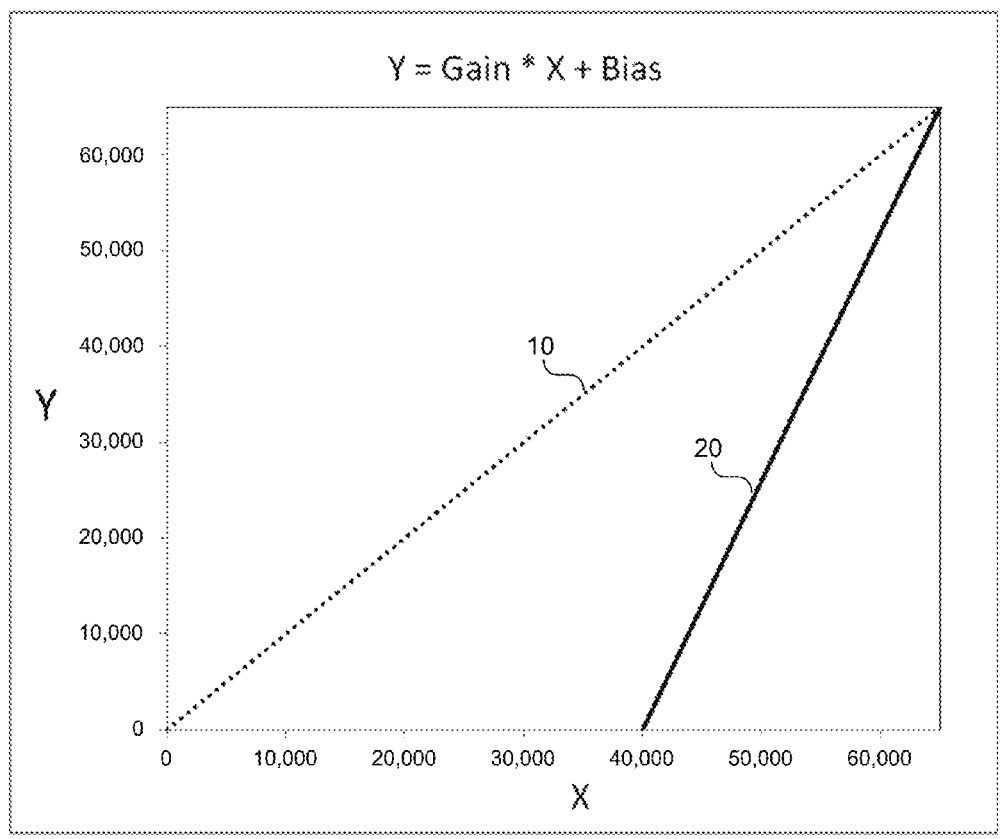
FIG. 2 shows one embodiment of an objective spectral stretching function applied to NIR data in accordance with an embodiment of the disclosed technology.

FIG. 2 shows one example of a function that can be used to create the objective spectral stretched NIR spectral data in order to be able to distinguish different types of vegetation in a digital aerial photo. In FIG. 2, the dotted line 10 shows a unity function where an input NIR data sample is equal to the output NIR data sample. The solid line 20 shown in FIG. 2 is one example of an objective spectral stretching function that is applied to input NIR spectral data to increase its variation. In the embodiment shown, NIR data having values less than 40,000 are treated as having a zero value, while NIR data having values from about 40,000 to 60,000 (about a 20K spread) are remapped to a range from 0 to 65,000 (e.g. a 65K spread). In this sense, the function operates to stretch the input NIR values that are greater than a threshold over an output range that is about three times the size of the input range.

One technique for determining the parameters (gain/slope and cut off) of the stretching function will be described in detail below.

In one embodiment, the objective NIR stretching function is a linear equation of the type $Y_{out}=Gain*X_{in}+Bias$, where $Y_{out}$ is the output NIR value and $X_{in}$ is the input NIR value. As can be seen from FIG. 2, NIR data having a value less than about 40,000 are treated as having a zero (0) value while input NIR data having values between 40,000-60,000 are re-mapped to output NIR values between 0 and 65,000.

In one embodiment, the gain of the linear stretching function is determined by $$\text{Gain} = \frac{F}{(X_{upper} - X_{lower})} \quad (1)$$

where F=the greatest possible radiometric value of NIR band that can be displayed. For example, F can be = 255 for 8-bit *NIR* data, or = 65,535 for 16-bit *NIR* data.

$X_{lower}$ is the lowest NIR data value for an item of interest (typically vegetation) in the image. The value of $X_{lower}$ is selected to eliminate un-interesting land covers/uses. In one embodiment, the value of for $X_{lower}$ is selected to be slightly less than the mean of the NIR data values in the image. For example, if an aerial photo contains a mix of hardwoods and conifers, then a value for $X_{lower}$ can be selected to be slightly less than the mean of the NIR data. Other man-made objects such as roads, buildings or natural objects such as bodies of water have NIR values that are below $X_{lower}$. If an input photo has a lot of lakes, rivers or man-made structures, then it may be necessary to adjust the value of $X_{lower}$ until the items of interest in the photo can be distinguished.

In one embodiment, the value $X_{upper}$ is the greatest radiometric value contained in the data from an image of the forest canopy in the NIR band. $X_{upper}$ can be some other values as well for various objects and $X_{upper}$ is always greater than $X_{lower}$.

In one embodiment, the value for the Bias parameters is selected as $$\text{Bias}=-X_{lower}*\text{Gain} \quad (2)$$

The parameters for the objective-based stretching function can be altered if the NIR color image created from the stretched NIR data does not distinguish between the types of vegetation. Once it appears that the different types of vegetation can be distinguished, the objective-based stretching function can be applied to the NIR data and the result divided by the red spectral data for the same pixel locations in order to create a OVI value for that pixel location.

FIG. 3A shows a NIR color image created by applying the objective spectral stretched NIR data to the red channel and red spectral data to the green channel and green spectral data to the blue channel. The NIR color image shown in FIG. 3A is typically a 24-bit color image (e.g. 8-bits for each of the red, green and blue channels). In contrast, the OVI values computed by dividing the objective spectral stretched NIR data by the red spectral data are typically re-organized into 8-bit values. Therefore, in one embodiment of the disclosed technology, a mean of the color used for pixels that map to the same OVI values is used to select what color should be used to represent a particular 8-bit OVI value.

In the NIR color image shown in FIG. 3A, many pixels will correspond to the same computed OVI value but will have slightly different colors. Therefore, in one embodiment, the mean RGB values for all the pixels in the NIR Color image that map to the same OVI value is used as the color for that OVI value.

Once the color of the OVI values has been determined, an image of the OVI values can be produced as shown in FIG. 3B. Once the image has been produced, a computer can identify all pixels that fall within a particular color range as being a particular type of vegetation. As will be appreciated, a computer can analyze the OVI color values in a memory without creating an image.

Figures 4A, 4B:
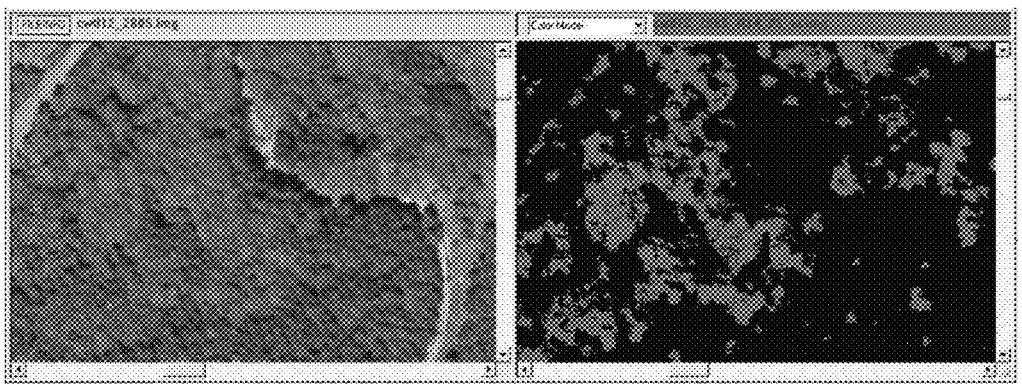
FIG. 4A is the same NIR color photo shown in FIG. 3A.
FIG. 4B is image created from OVI data created from objective spectral stretched NIR data that have been subjected to a threshold function in order to separate conifers from hardwoods in a digital aerial photo in accordance with an embodiment of the disclosed technology.

FIG. 4A is the same NIR color image shown in FIG. 3A. FIG. 4B shows an image of OVI values created from the objective spectral stretched NIR data where only the pixels in a range of color values that correspond to hardwoods are shown in a color other than black. By counting the total number of non black pixels in the image of FIG. 4B compared to the total number of pixels that the image could contain, it is possible to estimate the percentage of land or area that is occupied by hardwood trees in the image. Such a statistic can be used by foresters to estimate the value of such trees, or whether silviculture treatments should be applied (thinning, fertilizing etc.)

Figure 5:
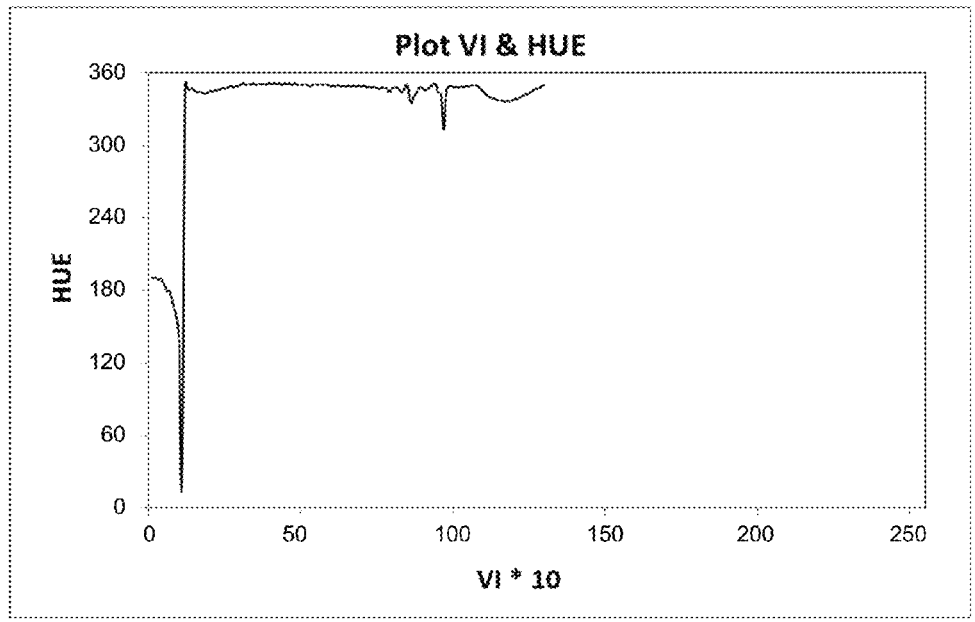
FIG. 5 illustrates a distribution of VI values created from non-stretched NIR data.

FIG. 5 illustrates a representative variation in simple VI values (times 10) computed from an image using un-stretched NIR data. As can be seen from the plot, some slight differences in simple VI values map to widely differing hue values while other differences cause almost no change in hue. Therefore separating different types of vegetation with simple VI values that are determined from unmodified NIR data can be difficult.

Figure 6:
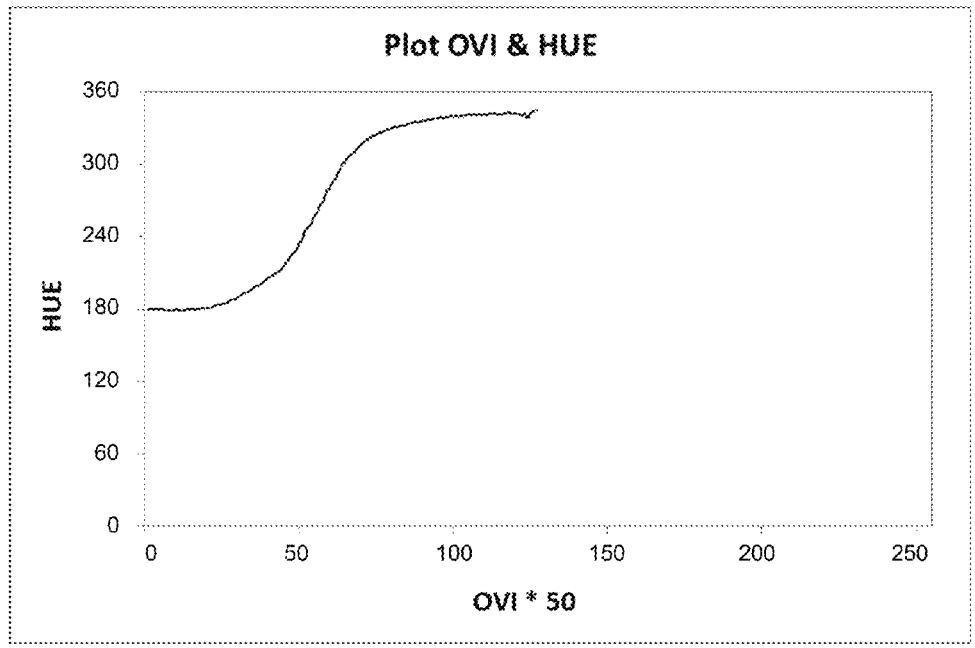
FIG. 6 illustrates a distribution of OVI values created from objective spectral stretched NIR data in accordance with an embodiment of the disclosed technology.

FIG. 6 shows a plot of a variation in OVI values (times 50) computed from the objective spectral stretched NIR data in accordance with the disclosed technology. As can be seen, hue values created from the OVI values vary smoothly over a color range. The distribution makes it much easier to separate different types of vegetation in the image.

Although the currently preferred embodiment of the technology is used to separate hardwoods from conifers, the technology could be used to separate other types of vegetation in a digital aerial photo.

Figure 7:
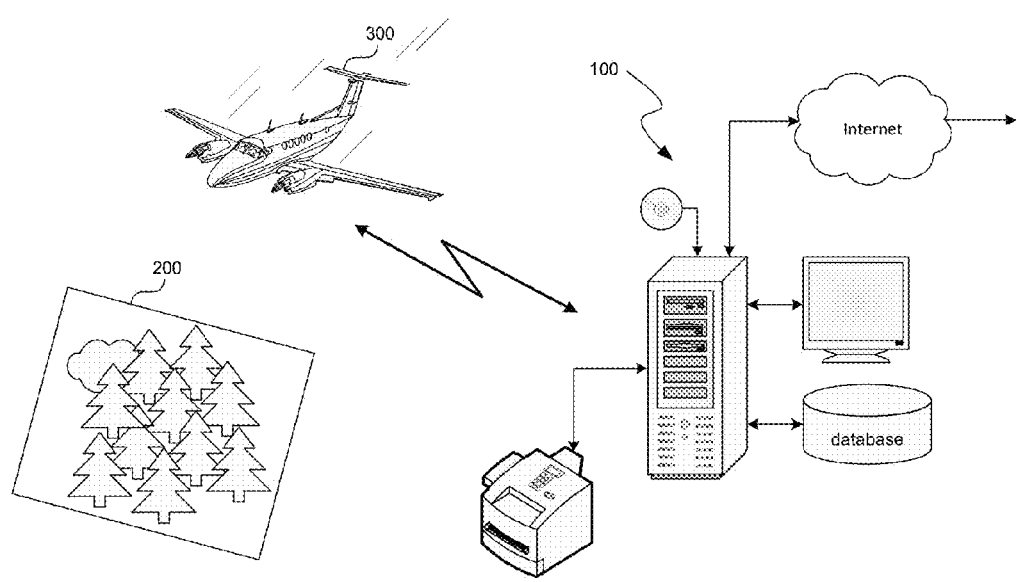
FIG. 7 illustrates a representative computer system that can be used to implement the disclosed technology.

FIG. 7 illustrates one embodiment of a computer system 100 that can operate to analyze digital aerial image data in accordance with the disclosed technology in order to identify different types of vegetation. The computer system 100 contains one or more processers that are configured to execute a series of program instructions that are stored in a non-transitory, computer readable media (hard drive, SSD, CD-ROM, flash drive, volatile or non-volatile memory of the like). Alternatively or in addition, the instructions may be received over a computer communication link such as the Internet. When executed, the processors receive or recall digital aerial photo data of an area of interest 200 that were obtained from an aircraft (airplane, helicopter, drone etc.) The computer system analyzes the NIR spectral data in the photo to compute initial parameters for the stretching function. The stretching function is applied to the NIR data and a NIR color image is created. The user or the computer analyzes the colors in the NIR color image to determine if different types of vegetation can be distinguished. The computer can estimate if different types of vegetation can be distinguished by determining the distribution of colored pixels in the NIR color image. If the distribution does not indicate that different types of vegetation are represented, then the parameters for the stretching function can be altered until the function can separate the types of vegetation.

Once a suitable stretching function has been determined, the one or more processors execute instructions to apply the stretching function to the NIR data for the remotely sensed photo. OVI values are then computed from the objective spectral stretched NIR data by dividing the objective spectral stretched NIR data by the red spectral data for the same pixels locations in the image. The resulting OVI values can then analyzed by the computer to separate different vegetation species by the color or magnitude of the OVI values. In one embodiment, a computer system identifies the different species of vegetation based on the color of the OVI value for a pixel in an image computed from the objective spectral stretched NIR data. For example, hardwoods are identified from OVI values that have a strong red component. Conifers can be identified by a computer by OVI values that have a stronger blue/green component. In some cases, the OVI values computed from the objective spectral stretched NIR data may be compared with ground truth data (data obtained by foresters in the field) in order to gain empirical data about what values of OVI values correlate with types of vegetation.

The resulting image or plot of OVI values can be analyzed by the computer system to inventory the different types of vegetation or to estimate their value etc. Results of the analysis can be displayed on a monitor, stored in database, printed on a printer or other output device or transmitted over the computer communication link to one or more other computers.

From the foregoing, it will be appreciated that specific embodiments of the invention have been described herein for purposes of illustration, but that various modifications may be made without deviating from the scope of the invention. For example, although the data for the area of interest is preferably received from an aerial photo, it will be appreciated that satellite images/photos could be used—provided the resolution is good enough to identify individual items of vegetation in the image. Accordingly, the invention is not limited except as by the appended claims.

We claim:

1. A computer system for producing an image in which conifers can be distinguished from hardwoods in a region of interest, comprising:
    a computer readable memory for storing programmed instructions that can be executed by a processor;
    one or more processors that are configured to execute the programmed instructions in order to:
        receive digital aerial image data for a region of interest including data in at least a near infrared (NIR) spectral band, a red spectral band and a green spectral band;
        stretch the near infrared (NIR) spectral band data by defining NIR spectral band data having values that are less than a threshold NIR value selected to eliminate unwanted land covers/uses in the digital aerial image as having a zero value and by mapping NIR spectral band data having values that are greater than the threshold NIR value into a larger output range of NIR values to increase a variation of NIR values that represent vegetation in the digital aerial image;
        apply the stretched NIR spectral band data to one of a red, green or blue channel and the red spectral band data to another of the red, green or blue channel and the green spectral data to another of the red, green or blue channel to define a number of colored pixels;
        compute objective vegetation index (OVI) values at locations corresponding to the colored pixels by dividing the stretched NIR spectral band data at each pixel location by the red spectral band data at the same pixel location;
        determine a color for each OVI value based on the average color of the colored pixels that correspond to the same OVI value; and
        produce a color image of the OVI values with their respective colors in which conifers can be distinguished from hardwoods in the region of interest.

2. A non-transitory computer readable medium with instructions stored thereon that are executable by a processor to produce an image in which conifers can be distinguished from hardwoods in a region of interest, wherein when executed, the instructions cause a processor to:
    receive digital aerial Image data for a region of interest including data in at least a near infrared (NIR) spectral band, a red spectral band and a green spectral band;
    stretch the near infrared (NIR) spectral band data by defining NIR spectral band data having values that are less than a threshold NIR value selected to eliminate unwanted land covers/uses in the digital aerial image as having a zero value and by mapping the NIR spectral band data having values that are greater than the threshold NIR value into a larger output range of NIR values to increase a variation of NIR values that represent vegetation in the digital aerial image;
    apply the stretched NIR spectral band data to one of a red, green or blue channel and the red spectral band data to another of the red, green or blue channel and the green spectral data to another of the red, green or blue channel to define colored pixels;

compute objective vegetation index (OVI) values at locations corresponding to the colored pixels by dividing the stretched NIR spectral band data at a pixel location by the red spectral band data at the same pixel location;

determine a color for each OVI value based on the average color of the colored pixels that map to the same OVI value; and produce a color image of the OVI values with their respective colors in which conifers can be distinguished from hardwoods in the region of interest.

3. A computer system for analyzing remotely sensed digital aerial image data in order to differentiate between hardwoods and conifers in a digital aerial image, comprising:

a computer readable memory for storing programmed instructions that can be executed by a processor;

one or more processors that are configured to execute the programmed instructions in order to:

receive digital aerial image data for a region of interest including data in at least a near infrared (NIR) spectral band and a red spectral band;

stretch the near infrared (NIR) spectral band data by defining NIR spectral band data having values that are less than a threshold NIR value selected to eliminate unwanted land covers/uses in the digital aerial image data as having a zero value and mapping NIR spectral band data having values larger than the threshold NIR value into a larger output range of NIR values to increase a variation of NIR values that represent vegetation in the digital aerial image;

divide the stretched NIR spectral band data for a location in the digital aerial image by the red spectral band data for the same location in the digital aerial image to define an OVI value; and display a color image of the OVI values in which pixels of the color image representing hardwoods are different than a color of the pixels representing conifers.

4. The computer system of claim 3, wherein the threshold NIR value is selected to be less than a mean of the NIR data values in the aerial image.

5. A non-transitory computer readable medium containing instructions that are executable by a processor to produce an image in which hardwoods are distinguishable from conifers, wherein the instructions cause the processor to:

receive digital aerial image data for a digital aerial image of a region of interest including data in at least a near infrared (NIR) spectral band and a red spectral band;

stretch the near infrared (NIR) spectral band data by defining NIR spectral band data having values that are less than a threshold NIR value selected to eliminate unwanted land covers/uses in the digital aerial image data as having a zero value and by mapping the NIR spectral band data having values larger than the threshold NIR value into a larger output range of NIR values to increase a variation of NIR values that represent vegetation in the digital aerial image data;

divide the stretched NIR spectral band data for a location in the digital aerial image by the red spectral band data for the same location in the digital aerial image to define an OVI value; and display an image of the OVI values as a number of pixels in which the color of the pixels representing hardwoods is different than a color of the pixels representing conifers.

6. The computer readable medium of claim 5, further comprising instructions executable by a processor to: compute a mean of the NIR data values in the digital aerial image data and select the threshold NIR value to be less than the mean.

\* \* \* \* \*